United States Patent
Drake, Jr.

(10) Patent No.: US 7,545,509 B2
(45) Date of Patent: *Jun. 9, 2009

(54) SYSTEM AND METHOD FOR ONLINE CONTROL OF PAPER ELASTICITY AND THICKNESS

(75) Inventor: Thomas E. Drake, Jr., Ft. Worth, TX (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/142,072

(22) Filed: May 9, 2002

(65) Prior Publication Data

US 2002/0185240 A1 Dec. 12, 2002

Related U.S. Application Data

(63) Continuation-in-part of application No. 09/416,399, filed on Oct. 12, 1999, now Pat. No. 6,657,733.

(60) Provisional application No. 60/091,229, filed on Jun. 30, 1998.

(51) Int. Cl.
*G01B 9/02* (2006.01)

(52) U.S. Cl. .................................................. 356/502

(58) Field of Classification Search ................. 356/432, 356/502
See application file for complete search history.

(56) References Cited

U.S. PATENT DOCUMENTS

| | | | |
|---|---|---|---|
| 3,911,733 A | 10/1975 | Bhuta et al. ...................... 73/88 |
| 3,992,627 A | 11/1976 | Stewart ....................... 250/312 |
| 4,349,112 A | 9/1982 | Wilks et al. .................. 209/538 |
| 4,355,538 A | 10/1982 | Hall ............................. 73/811 |
| 4,388,830 A | 6/1983 | Narushima et al. ............. 73/579 |
| 4,393,711 A | 7/1983 | Lapides ........................ 73/592 |
| 4,422,177 A | 12/1983 | Mastronardi et al. ........... 378/17 |
| 4,659,224 A | 4/1987 | Monchalin ................... 356/352 |
| 4,803,639 A | 2/1989 | Steele et al. ................. 364/507 |
| 4,809,308 A | 2/1989 | Adams et al. .................. 378/99 |
| 4,841,460 A | 6/1989 | Dewar et al. ............ 364/571.02 |
| 5,014,293 A | 5/1991 | Boyd et al. .................. 378/197 |
| 5,065,630 A | 11/1991 | Hadcock et al. ............... 73/802 |
| 5,113,079 A | 5/1992 | Matulka ...................... 250/550 |
| 5,119,408 A | 6/1992 | Little et al. ..................... 378/4 |
| 5,122,672 A | 6/1992 | Mansour ..................... 250/571 |
| 5,140,533 A | 8/1992 | Celette ........................ 364/559 |

(Continued)

OTHER PUBLICATIONS http://metwww.epfl.ch/Brillouin/physique_brillouinE.thm; "Physics of Brillouin scattering"; Mar. 26, 2002; 3 pages.

(Continued)

*Primary Examiner*—Hwa (Andrew) S Lee
(74) *Attorney, Agent, or Firm*—Bracewell & Giuliani LLP

(57) ABSTRACT

The invention is directed to a system and method for implementing process control for paper elasticity and thickness using sonic NDE techniques. The system may, for example, generate ultrasound waves in a test object during the manufacturing process. A detector such as an interferometer may be used to detect the ultrasound waves. An interpreter or analyzer may determine the thickness and/or elastic properties of paper from the waves. Then, a control system may determine and implement an appropriate control action on the process.

20 Claims, 5 Drawing Sheets

U.S. PATENT DOCUMENTS

| | | | | |
|---|---|---|---|---|
| 5,295,073 | A | | 3/1994 | Celette .................. 364/424 |
| 5,319,567 | A | | 6/1994 | Ebenstein .............. 364/474.34 |
| 5,384,717 | A | | 1/1995 | Ebenstein .................. 364/560 |
| 5,442,572 | A | | 8/1995 | Kiridena et al. ............. 364/560 |
| 5,490,195 | A | | 2/1996 | Berkley ..................... 378/72 |
| 5,541,856 | A | | 7/1996 | Hammermeister .......... 364/552 |
| 5,552,984 | A | | 9/1996 | Crandall et al. ........ 364/424.03 |
| 5,574,226 | A | | 11/1996 | Reuther et al. ................ 73/669 |
| 5,604,592 | A | * | 2/1997 | Kotidis et al. ............... 356/493 |
| 5,623,307 | A | | 4/1997 | Kotidis et al. ............... 356/351 |
| 5,637,812 | A | | 6/1997 | Baker et al. ................ 73/865.6 |
| 5,672,830 | A | | 9/1997 | Rogers et al. ................. 73/597 |
| 5,724,138 | A | * | 3/1998 | Reich et al. .................. 356/492 |
| 5,848,115 | A | | 12/1998 | Little et al. ..................... 378/4 |
| 5,982,482 | A | | 11/1999 | Nelson et al. ............ 356/237.1 |
| 6,016,202 | A | * | 1/2000 | Fuchs et al. .................. 356/432 |
| 6,023,985 | A | | 2/2000 | Fournier .................... 73/865.6 |
| 6,047,041 | A | | 4/2000 | Ellinger ....................... 378/58 |
| 6,065,348 | A | | 5/2000 | Burnett ........................ 73/801 |
| 6,078,397 | A | | 6/2000 | Monchalin et al. ........... 356/357 |
| 6,092,419 | A | | 7/2000 | Dixon et al. .................. 73/602 |
| 6,108,087 | A | | 8/2000 | Nikoonahad et al. ........ 356/359 |
| 6,128,081 | A | * | 10/2000 | White et al. ................. 356/503 |
| 6,205,240 | B1 | | 3/2001 | Pietrzak et al. ............. 382/152 |
| 6,220,099 | B1 | | 4/2001 | Marti et al. .................... 73/633 |
| 6,322,666 | B1 | | 11/2001 | Luontama et al. ........... 162/198 |
| 6,360,621 | B1 | | 3/2002 | Eldred et al. ............... 73/865.6 |
| 6,378,387 | B1 | | 4/2002 | Froom ....................... 73/865.8 |
| 6,466,643 | B1 | | 10/2002 | Bueno et al. ................... 378/58 |
| 6,571,008 | B1 | | 5/2003 | Bandyopadhyay et al. .. 382/154 |
| 6,637,266 | B1 | | 10/2003 | Froom ......................... 73/583 |

OTHER PUBLICATIONS

Using Light to Measure Temperature and Strain; Report No. 6; date unknown; 4 pages.

"Temperature and annealing dependence of the longitudinal ultrasonic velocity in aluminum alloys"; Johnson, Ward et al.; J. of Mater. Res., vol. 8, No. 7, p. 1558; 1996.

http://nte-serveur.univ-lyon1.fr/nte/spectroscopie/resumESOPS/Alig1.htm; "Ultrasonic spectroscopy For characterization of Polymeric Materials"; I. Alig and D. Lellinger; Mar. 26, 2002; 2 pages.

"Temperature Dependence of Ultrasonic Velocity Using Diffuse Fields; Implications for Measurement of Stress"; Richard Weaver and Oleg Lobkis; Department of Theoretical and Applied Mechanics; University of Illinois; reprint QNDE 2000; 8 pages.

Spacemaker, Jun. 19, 1997, Bates 000326 through 000327.

Civilian Personnel Position Description, Department of the Air Force; Jul. 10, 1989, Bates 000328 through Bates 000332.

Aviation Week & Space Technology, Mar. 13, 1989, Bates 000333 through Bates 000336.

UltraOptec, Laser Ultrasonic System, 1999 IEEE, Bates 000337 through Bates 000340.

J.W. Bader, et al., Laser Ultrasonics or Alternative NDI Composite Defect, Nov. 20, 1990, Bates 000342 through Bates 000446.

Douglas A. Froom, Statement of Work for Advanced Ultrasonic Component Inspection System, Jul. 14, 1993, Bates 000447 through 000490.

Award of Contract from Department of the Air Force, Aug. 11, 1993, Bates 000491 through Bates 000492.

UltraOptec, LUIS Phase 3 Acceptance Test Report, Feb. 16, 1996, Bates 000493 through Bates 000501.

Spacemaker, Feb. 22, 1996, Bates 000502.

NTIAC Newsletter; vol. 27, No. 5, Sep. 2002, 5 pp.

Froom, Douglas A., et al.; Solving Problems with Advanced Technology, 1999 IEEE, 4 pp.

Alkire, M.G., Department of the Air Force Memo regarding Construction Project Data; May 7, 1982, Bates 000010 through Bates 000068.

U.S. Air Force, Military Construction Project Data, Apr. 14, 1982, Bates 000074 though Bates 000129.

U.S. Air Force, Attachment I to Request for Environmental Impact Analysis, Dec. 2, 1982, Bates 000130 through Bates 000167.

Stanghellini, Frank D., Department of the Air Force Memo regarding Criteria Changes, Jan. 9, 1985, Bates 000168 through Bates 000214.

Metro Today, The Sacramento Union; May 12, 1983, Bates 000215 through Bates 000216.

Letter Contract Between Department of the Air Force and Par Systems Corp., Aug. 3, 1984, Bates 000217 through Bates 000312.

Timeline and Equipment List for Contract Between Department of the Air Force and Par Systems Corp., Aug. 3, 1984, Bates 000313 through Bates 000325.

* cited by examiner

SYSTEM AND METHOD FOR ONLINE CONTROL OF PAPER ELASTICITY AND THICKNESS

RELATED APPLICATIONS

This application claims the benefit of, incorporates by reference, and is a Continuation-In-Part of Non-Provisional patent application Ser. No. 09/416,399 filed on Oct. 12, 1999, entitled "METHOD AND APPARATUS FOR DETECTING ULTRASONIC SURFACE DISPLACEMENTS USING POST COLLECTION OPTICAL AMPLIFICATION" to Thomas E. Drake. Non-Provisional patent application Ser. No. 09/416,399 in turn claims benefit to U.S. Provisional Application No. 60/091,229 filed on Jun. 30, 1998. This application incorporates by reference the prior U.S. Provisional Application No. 60/091,240 filed on Jun. 30, 1998 entitled "METHOD AND APPARATUS FOR ULTRASONIC LASER TESTING" to Thomas E. Drake. This application is related to and incorporates by reference: Non-Provisional patent application Ser. No. 10/142,071, filed on May 9, 2002, entitled "SYSTEM AND METHOD FOR CONTROL OF PAINT THICKNESS" to Thomas E. Drake; Non-Provisional patent application Ser. No. 10/142,073 entitled "SYSTEM AND METHOD FOR CONTROLLING TUBE THICKNESS" to Thomas E. Drake; and Non-Provisional patent application Ser. No. 10/142,178, filed on May 9, 2002, entitled "SYSTEM AND METHOD FOR CONTROLLING WAFER TEMPERATURE".

TECHNICAL FIELD OF THE INVENTION

This invention relates in general to non-destructive examination techniques. More specifically, the invention relates to control using ultrasound testing methods in paper manufacturing.

BACKGROUND OF THE INVENTION

Non-destructive examination (NDE) of objects may be used to test for defects in manufactured parts. NDE provides a method of examination that limits damage the tested part. As such, parts may be examined before they are placed in service. Further, used parts may be examined for flaw or defects resulting from use.

However, many typical techniques are slow. Further, the results of the tests are difficult to interpret and typically require an human observer. Typically, these techniques require a human observer to perform analysis. Therefore, the techniques are not automated.

These typical techniques may also require contact with the surface of the tested part. In many processes, parts or objects are moving through the process at great speeds. In other processes, contact with the part or object may be limited because of drying or annealing surface films. Further, contact with the part may be limited by other process variables.

As such, these techniques are not suitable for use in process control. The slow testing time may not provide enough information for process control applications. Further, a lack of automation in the analyzing the results limits applicability to process control. In addition, contact with the part may not be suitable, preventing the technique from use in the process.

For example, in paper manufacturing, specification for paper include thickness and elastic properties. Process parameters must be adjusted to compensate for changes in pulp quality, paper grade, moisture, humidity, temperature, and fiber content, among others. Typical methods for testing paper elastic properties require cutting samples from a roll of paper after production. These methods can take 40 minutes to acquire results. As such, there may be a 40 minute or more delay in changing the process. This delay may result in a large quantity of off-spec paper which must either be sold as a cheaper grade, recycled, or discarded. During processing, the paper may travel at great speeds. These speed limit contact with the paper and thus exclude many typical measuring techniques.

As such, many typical testing techniques suffer from deficiencies in speed and automation. Many other problems and disadvantages of the prior art will become apparent to one skilled in the art after comparing such prior art with the present invention as described herein.

SUMMARY OF THE INVENTION

Aspects of the invention may be found in an apparatus for determining thickness and/or elastic properties of paper. The apparatus may have a sonic energy generator, one or more detectors and an interpreter. The sonic energy generator may, for example, be a laser generator directing a beam of coherent electromagnetic energy at an object. From the impinging energy, sonic energy waves may be generated about the object or along the surface of the object, among others. The one or more detectors may detect and/or measure the sonic energy waves. An interpreter may then be used to determine the thickness and/or elastic properties.

Aspects of the invention may also be found in a method for determining the thickness and/or elastic properties of paper. Sonic energy waves may be generated about a test object using a sonic energy generator. The sonic energy waves may be detected and/or measured by a sonic energy detector. The thickness and/or elastic properties may be determined by an interpreter.

Another aspects of the invention may be found in an apparatus for process control of the thickness and/or elastic properties of paper. The apparatus may have a sonic energy generator, one or more detectors, and a control system. The sonic energy generator may, for example, be a laser generator directing a beam of coherent electromagnetic energy at an object. From the impinging energy, sonic energy waves may be generated about the object or along the surface of the object, among others. The one or more detectors may detect and/or measure the sonic energy waves. The control system may determine what action may be taken to achieve and/or maintain an aspect of the object near or about a set point.

A further aspects of the invention may be found in a method for process control of the thickness and/or elastic properties of paper. Sonic energy waves may be generated about a test object using a sonic energy generator. The sonic energy waves may be detected and/or measured by a sonic energy detector. An action may be determined, which may achieve and/or maintain an aspect of the object near or about a set point.

Another aspects of the invention may be found in a control system. The control system may have an analyzer, a controller, and interfaces. An interface may receive data from a sonic energy detector. The analyzer may determine and/or generate a signal relating to the thickness and/or elastic properties of the paper. The controller may use the signal from the analyzer to determine an appropriate control action. The action may be implemented using an interface to the process. Furthermore, the control system may have one or more modelers, one or more stored results, one or more threshold values, and one or more algorithms. Each of these may or may not be used by the analyzer or controller in performing their respective function.

As such, a system for control of a paper manufacturing process is described. Other aspects, advantages and novel features of the present invention will become apparent from the detailed description of the invention when considered in conjunction with the accompanying drawings.

BRIEF DESCRIPTION OF THE DRAWINGS

For a more complete understanding of the present invention and advantages thereof, reference is now made to the following description taken in conjunction with the accompanying drawings in which like reference numbers indicate like features and wherein.

Corresponding reference numerals indicate corresponding parts throughout the several views of the drawings.

DETAILED DESCRIPTION OF THE PREFERRED EMBODIMENT

Sonic energy traverses through objects with varying characteristics. These characteristics may include speed, wave type, frequency spectrum, amplitude. Further the sonic energy may partially reflect from surfaces or inconsistencies. Waves may also translate across a surface.

The characteristics of the sonic energy may be a function of various aspects of the substance about which the sonic energy travels. These aspects may include elastic properties, internal structure, flaws, thickness of material, and layers of film, among others. These aspects may be a further function of temperature and moisture content, among others. As such, sonic energy waves may be used to aid in determining aspects of the material for use in process control.

In one exemplary embodiment, the thickness and elastic properties may be determined by measuring ultrasounds characteristics. The elastic properties may include bending stiffness and/or out-of-plane shear rigidity, among others. The ultrasound characteristics may include velocity and attenuation.

Figure 1:
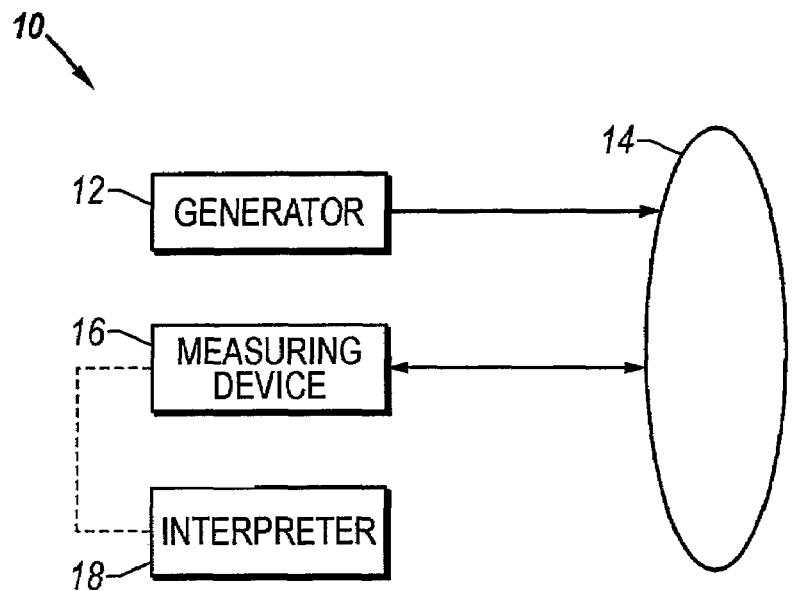
FIG. 1 is a schematic block diagram the system, according to the invention.

FIG. 1 depicts a system, according to the invention. In the system 10, a sonic energy generator 12 may generate sonic energy waves in a test object 14. The system may also have a detector or measuring device 16. The detector or measuring device 16 may detect or measure the sonic energy waves. An interpreter 18 may be used to determine the sonic wave characteristic, material aspect and/or value of a variable from which the material aspect depends.

The sonic energy generator 12 may take various forms. These forms may include a coherent electromagnetic energy source, a laser, a plasma generator, and a transducer, among others. Further, the coherent electromagnetic energy source and/or laser may take various forms. These forms may include a $CO_2$ laser, a q-switch YAG laser, a mid-IR laser, and other solid-state and/or gas lasers, among others. However, various lasers may be envisaged.

The measuring device 16 may take various forms. These forms may include an interferometer, a gas-coupled laser acoustic detector, and a transducer, among others. Further, the interferometer may take the form of a Mach-Zender, Fabry-Perot, Dual Differential Confocal Fabry-Perot, Two Wave Mixing, photorefractive or other interferometer. Other interferometers and sonic energy detection methods may be used as well. A generator may be used to generate coherent electromagnetic energy for use in the interferometer. One exemplary embodiment is a long pulse ND:YAG laser. However, other lasers may be used.

The interpreter 18 may take various forms. These forms may include a computer, workstation, handheld, computational circuitry, analog device, or digital alarm, among others. Further, the interpreter may compare the signal to an expected signal, determine the location of one or more peaks, determine the amplitude of one or more peaks, and transform the signal, among others. The interpreter may operate on the signal in a time domain or frequency domain, among others. Further, the interpreter may determine the velocity of the wave and, with the velocity, determine the elastic properties from a correlation or model.

In one exemplary embodiment, the system may take the form of a laser ultrasound system. The laser ultrasound system may use a $CO_2$ laser. A beam from the laser may be direct to the object. This beam may be directed through fiber optic cable. A ND:YAG laser may direct a beam of coherent electromagnetic energy toward the object. The beam may, at least in part, reflect from the object with an altered characteristic indicative of the sonic energy. Part of the reflected beam may be collected by the collection optics of a dual differential confocal Fabry-Perot interferometer. However, a photorefractive, two wave mixing, or other interferometer may be used.

In this exemplary embodiment, the interferometer may generate a signal. The signal may be interpreted by the interpreter or analyzer. From the signal, the interpreter or analyzer may determine the thickness and/or elastic properties.

Figure 2:
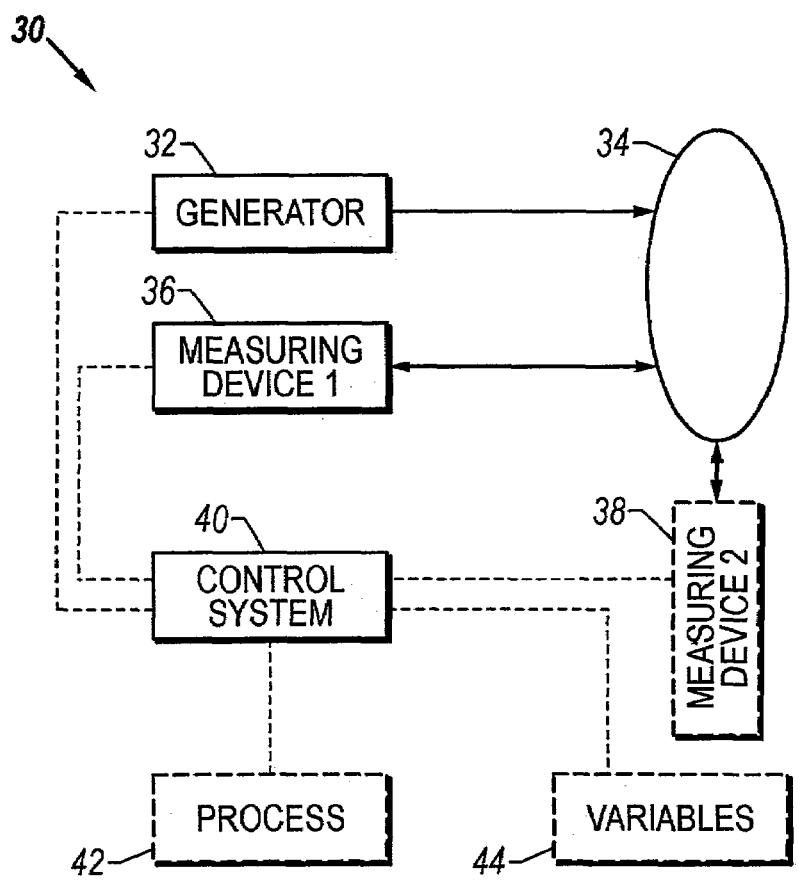
FIG. 2 is a schematic block diagram of the system, according to the invention.

FIG. 2 is a schematic block diagram of a system, according to the invention. The system 30 may have a generator 32, one or more measuring devices 36 and 38, and a control system 40. The control system 40 may or may not be coupled to generator 32 and the one or more measuring devices 36 and 38. The system 30 may or may not also be coupled to the process 42 and other variables 44. However, various configurations may be envisaged. These elements may be together, separate, or in various combinations, among others.

The generator 32 may generate sonic energy waves in the object 34. The one or more detectors 36 and 38 may detect the sonic energy waves. The control system 40 may receive signals from the one or more detectors 36 and 38. From the signals, the control system 40 may determine an appropriate control action. Further, the control system 40 may implement the control action. The control action may include manipulating characteristics associated with the generator, altering characteristics associated with the measuring device, and manipulating process parameters, among others. The control system may also use other process measurements, parameters, and variables 44 in determining the control action.

The generator 32 may take various forms. These forms may include a coherent electromagnetic energy source, a laser, a plasma generator, and a transducer, among others. Further, the coherent electromagnetic energy source and/or laser may take various forms. These forms may include a $CO_2$ laser, a q-switch YAG laser, a mid-IR laser, and other solid-state and/or gas lasers, among others. However, various lasers may be envisaged.

The one or more measuring devices 36 and 38 may take various forms. These forms may include an interferometer, a gas-coupled laser acoustic detector, and a transducer, among others. Further, the interferometer may take the form of a Fabry-Perot, Dual Differential Confocal Fabry-Perot, Two Wave Mixing, photorefractive or other interferometer. Other interferometers and sonic energy detection methods may be used as well. A coherent electromagnetic energy source may be used to generate coherent electromagnetic energy beam for use with the interferometer. One exemplary embodiment is a long pulse ND:YAG laser. However, other lasers may be used.

The control system 40 may take various forms. These forms may include digital control, analog control, or distributed control system, among others. Further, the control system 40 may or may not be implemented on a computational circuitry, computer, or workstation, among others.

The variables 44 may take various forms. These forms may include known process parameters, other measured values, control parameters, model parameters, algorithm parameters, and set points, among others.

For example, a laser generator may be used to generator and direct a laser beam toward a paper sheet as it moves through production. As the beam impinges the paper sheet, sonic energy waves such as ultrasonic waves may be generated. One or more beams may be directed at the sheet for use with one or more interferometers. The one or more beams may reflect from the sheet with a modulated characteristic associated with the sonic energy waves. The one or more interferometers may measure at least part of the beams as they reflect from the sheet. The interferometers may send a signal to a distributed control system. The distributed control system may determine and implement an action such as changing a process parameters. This process parameter may be an extrusion pressure, an extruder temperature, a laminator parameters, a tension, a roller speed, or any combination of parameters, among others.

In this manner real time control may be implemented for paper manufacturing. With this control, product specifications may be more closely monitored, waste may be reduced, a consequently costs and profits may increase.

Figure 3:
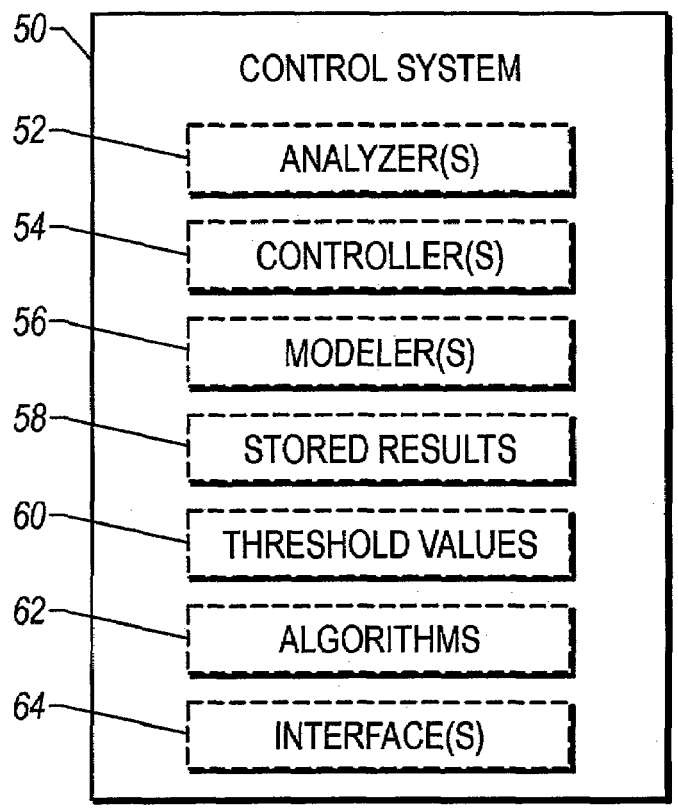
FIG. 3 is a block schematic diagram of an exemplary embodiment of a control system as seen in FIG. 2.

FIG. 3 is a block diagram of an exemplary embodiment of a control system for use in the system as seen in FIG. 2. The control system 50 may have analyzers 52, controllers 54, modelers 56, stored results 58, threshold values 60, algorithms 62, and interfaces 64. However, the control system may have some, all, or none of these elements. Further, these elements may be separate, together, or in various combinations, among others.

The analyzer 52 may perform various functions. These functions may include estimating parameters, determining location and/or amplitude of peaks, comparing location and/or amplitude of peaks to a value, and/or comparing the signals to expected signals. Further the analyzer 52 may perform these functions in time domain and/or frequency domain. In addition, the analyzer may utilize the output of the process, other variables, the modeler 56, stored results 58, and threshold values 60, among others.

The controller 54 may perform various functions. These functions may include determining an action in response to an output from the analyzer 52. The action may relate to manipulating process parameters, generator parameters, measuring device parameters, and other variables, among others. Further, the action may be an alert, alert, or message, among others. In addition, the controller 54 may utilize values of process and other variables in determining a control action.

The modeler 56 may take various forms. These forms may include a CAD model, a propagation model, and a control model, among others. Further, the model may use parameters and other outputs from the process, other variables, stored results, threshold values, process setting, and set points, among others, in performing its function. In addition, the model may interact with the controller 54 and/or the analyzer 52, to aid in the function of those units.

The stored results 58 may take various forms. These forms may include previous results, process data, expected results, modeler 56 output, analyzer 52 output, controller 54 output, and user data, among others. The stored results may or may not be accessed by the process, controller 54, analyzer 52, and modeler 60, among others.

The threshold values 60 may be used in various manners. These manners may include comparison with peaks, set points, model output, process parameters, and other variables, among others. Further, these threshold values 60 may be determined automatically or set by a user.

The algorithms 62 may direct the performance of various functions. These functions may include controller, generator, measuring device, and process functionality, among others.

The interfaces 64 may take served to communicate with various devices. These devices may include the process, generator, measuring devices, other equipment, network interfaces and user interfaces, among others.

For example, a control system may interface with a generator and a measuring device associated with paper manufacturing. For example, a control system may direct a laser generator to produce a beam and direct the beam at a sheet of paper moving through the manufacturing process. The beam may impinge the sheet and cause a sonic energy wave such as an ultrasonic waver. The control system may direct a laser associated with an interferometer to produce and direct a beam toward the sheet. An interferometer may collect scattered light associated with the beam and having characteristics associated with the sonic energy waves. The interferometer may send a signal to the control system. The signal may be processed by the analyzer to derive a signal indicative of the thickness and/or elastic properties. For example, the analyzer may regress parameters associated with the thickness and/or elastic properties from the data. Alternately, the analyzer may determine velocity and compare the velocity with a correlation or model output. In another example, regressed parameters, peak locations, and/or peak amplitudes may be compared with threshold values and/or acceptable ranges of values. The analyzer may also use information associated with the process such as the speed of the paper sheet. However, various methods may be used to determine the analyzer output.

The analyzer output may be utilized by a controller to determine an appropriate change to the process. These changes may include adjusting a process parameter such as an extrusion pressure, an extruder temperature, a laminator parameters, a tension, a roller speed, or any combination of parameters, among others.

Figure 4:
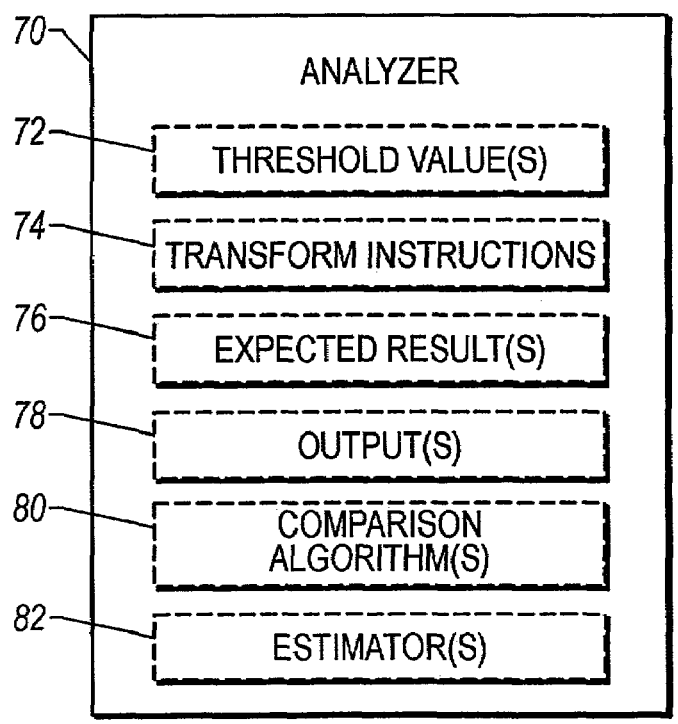
FIG. 4 is a block schematic diagram of an exemplary embodiment of an analyzer as seen in FIG. 3.

FIG. 4 is a block diagram of an exemplary embodiment of an analyzer for use in the controller of FIG. 3. Further, the analyzer may act as an interpreter as seen in FIG. 1. The analyzer 70 may or may not have threshold values 72, transform instructions 74, expected results 76, outputs 78, comparison algorithms 80, and estimators 82. However, the analyzer 70 may have all, some, or none of the elements. Further, these elements may be separate, together, or in various combinations, among others.

The analyzer may receive data from other components in the control system, the measuring devices, process, or other variables, among others. The analyzer may function to analyze these signals together, separately, or in various combinations.

The transform instructions 74 may direct the implementation of various functions. These forms may include scaling and Fourier transforms, among others.

The expected results 76 may take various forms. These forms may include an expected time domain sonic wave, a frequency domain sonic wave response, a location of one or more peaks in a time domain and/or frequency domain data, an amplitude of one or more peaks in a time domain and/or frequency domain data, the output of a wave propagation model, a past result, and expected parameters of a model, among others. However, other expected results may be envisaged.

The comparison algorithms may implement various functions. These functions may include comparison between the signal and an expected result or threshold values. The comparison may be performed in a frequency and/or time domain, among others. Further, these functions may include comparing peak amplitudes with an expected amplitude or threshold value, subtracting an expected result from a signal, and compare an parameter determined by the estimator 82 to a threshold or expected value, among others.

The estimator 82 may function to determine parameters associated with the data from the one or more measuring devices. For example, the estimate may fit a line or some other curve to the data. The estimator 82 may, alternately, regress parameters of a model from the data. Further, the estimator 82 may use various methods and algorithms for fitting and/or regressing. Further, the estimator 82 may use signals and inputs from the control system, process, measuring devices, generator, and other variables, among others, in regressing the parameters.

The outputs 78 may be outputs to other components of the control system. For example, the outputs may direct the results of the comparison algorithms 80, estimators 82, or transform instructions 74, among others, to other components of the control system such as the modeler, controller, interfaces, stored results, or other analyzers, among others.

For example, the analyzer may function to determine an output associated with thickness and/or elastic properties. In one exemplary embodiment, the analyzer may regress parameters associated with the thickness and/or elastic properties from one or more signals from one or more measuring devices. The analyzer may either compare these parameters to an expected value or range or send the parameter to a controller. In another example, the analyzer may determine the locations of one or more peaks in a time domain and correlate the peak to velocity, thickness, and/or elasticity. However, various methods may be envisaged.

In addition, the analyzer may function to filter distortions caused by machine vibration or other vibrations associated with the process. The analyzer may perform this function by a frequency filter. However, various other methods may be envisaged.

Figure 5:
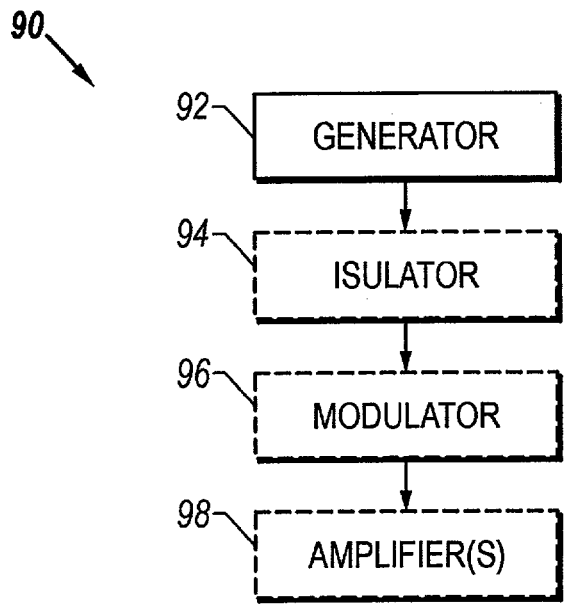
FIG. 5 is a schematic block diagram of an exemplary embodiment of the generator as seen in FIG. 1.

FIG. 5 is an schematic block diagram of an exemplary embodiment of a laser as seen in FIG. 1 and FIG. 2. The laser 90 may be used as a sonic energy generator or a beam generator for an interferometer, among others. The laser 90 may, for example, have a pulse generator 92 that generates a pulse. The pulse may traverse an isolator 94, a modulator 96, and one or more amplifiers 98. However, these elements may or may not be included. Further, these elements may be separate, together, or in any combination, among others.

The pulse generator 92 may take various forms. These forms may take the embodiments described above, diode generators, and a VCSEL, among others. The isolator 94 may function to prevent backscattering of light into the pulse generator.

The modulator 96 may take various forms. These forms may include electro-optic modulators, and acousto-optic modulators, among others. Further, the modulator 96 may function to alter wave characteristics such as pulse length, pulse frequency profile, phase and pulse amplitude, among others. This function may or may not be implemented in conjunction with the amplifiers 98.

The amplifiers 98 may take various forms. These forms may include pumped slabs, cylinders, and zigzag slabs, among other. The amplifiers may function to increase the amplitude of the laser pulse. In addition, the amplifiers may be configured to alter other wave characteristics such as frequency profile, and pulse length, among others.

Figure 6:
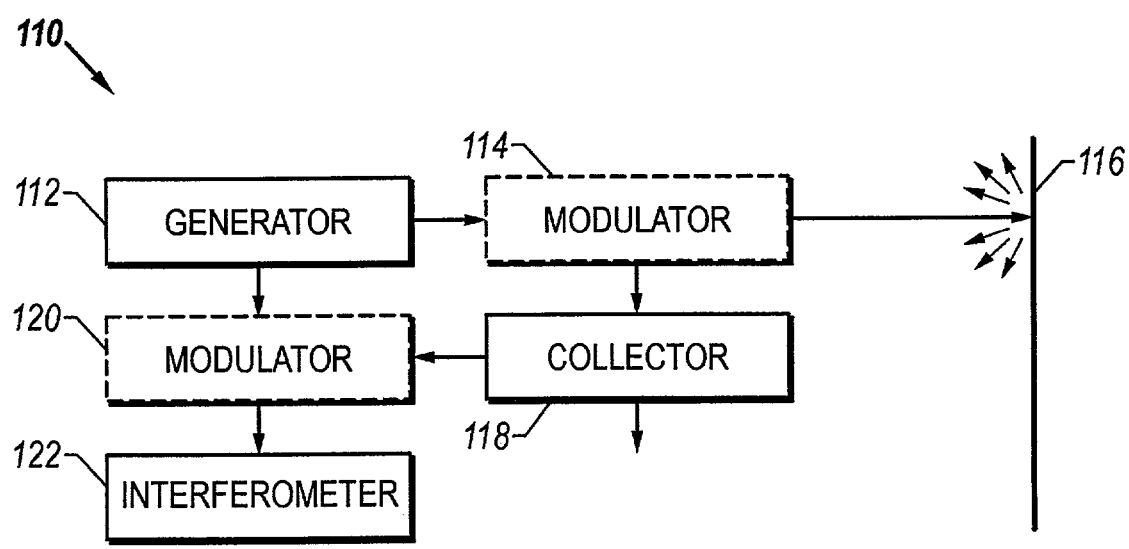
FIG. 6 is a schematic block diagram of an exemplary embodiment of a measuring device as seen in FIG. 1.

FIG. 6 is a schematic block diagram of a exemplary embodiment of a measuring device or detector as seen in FIGS. 1 and 2. The measuring device 110 may have a generator 112, a modulator 114, a collector 118, a modulator 120, and an interferometer. These elements may or may not be included. Further, these elements may be together, separate, or in various combinations, among others.

The generator 112 may generate a coherent electromagnetic energy beam. The beam may or may not be modulated with modulator 114. The beam may be directed to an object 116. A modulated beam may reflect from the object 116 with a characteristic associated with sonic energy waves about the object 116. Part of the modulated beam may be collected in a collector 118. The collected beam may or may not be directed to a modulator 120. The beam may be directed to an interferometer 122 wherein the beam may be detected and measured.

The generator 112 may take various forms. These forms may include a coherent electromagnetic energy source or a laser, among others. Further, the coherent electromagnetic energy source and/or laser may take various forms. These forms may include a $CO_2$ laser, a q-switch YAG laser, a mid-IR laser, an ND:YAG laser and other solid-state and/or gas lasers, among others. However, various lasers may be envisaged.

The modulator 114 may take various forms. These forms may include electro-optic modulators, and acousto-optic modulators, among others. Further, the modulator 114 may alter a characteristic of the beam such as frequency profile, pulse length, phase and pulse amplitude. This function may be performed in conjunction with an amplifier. For example, the modulator 114 may alter the wave characteristic to enhance reflection, compensate for beam attenuation, and compensate for Doppler effects relating to object movement or a scanning motion, among others.

The collector 118 may function to collect part of the reflected modulated beam. The collector may have various apertures.

The modulator 120 may take various forms. These forms may include electro-optic modulators, and acousto-optic modulators, among others. Further, the modulator 114 may alter a characteristic of the beam such as frequency profile, pulse length, phase and pulse amplitude. For example, the modulator 114 may alter the wave characteristic to enhance detection, compensate for beam attenuation, and compensate for Doppler effects relating to object movement or a scanning motion, among others.

The interferometer 122 may take various forms. These forms may include those listed above, among others. These forms may include a Fabry-Perot, dual differential confocal Fabry-Perot, two wave mixing, and photo-refractive interferometer, among others. The interferometer may send a signal relating to the sonic energy wave to an analyzer, control system, or interpreter, among others.

Figure 7:
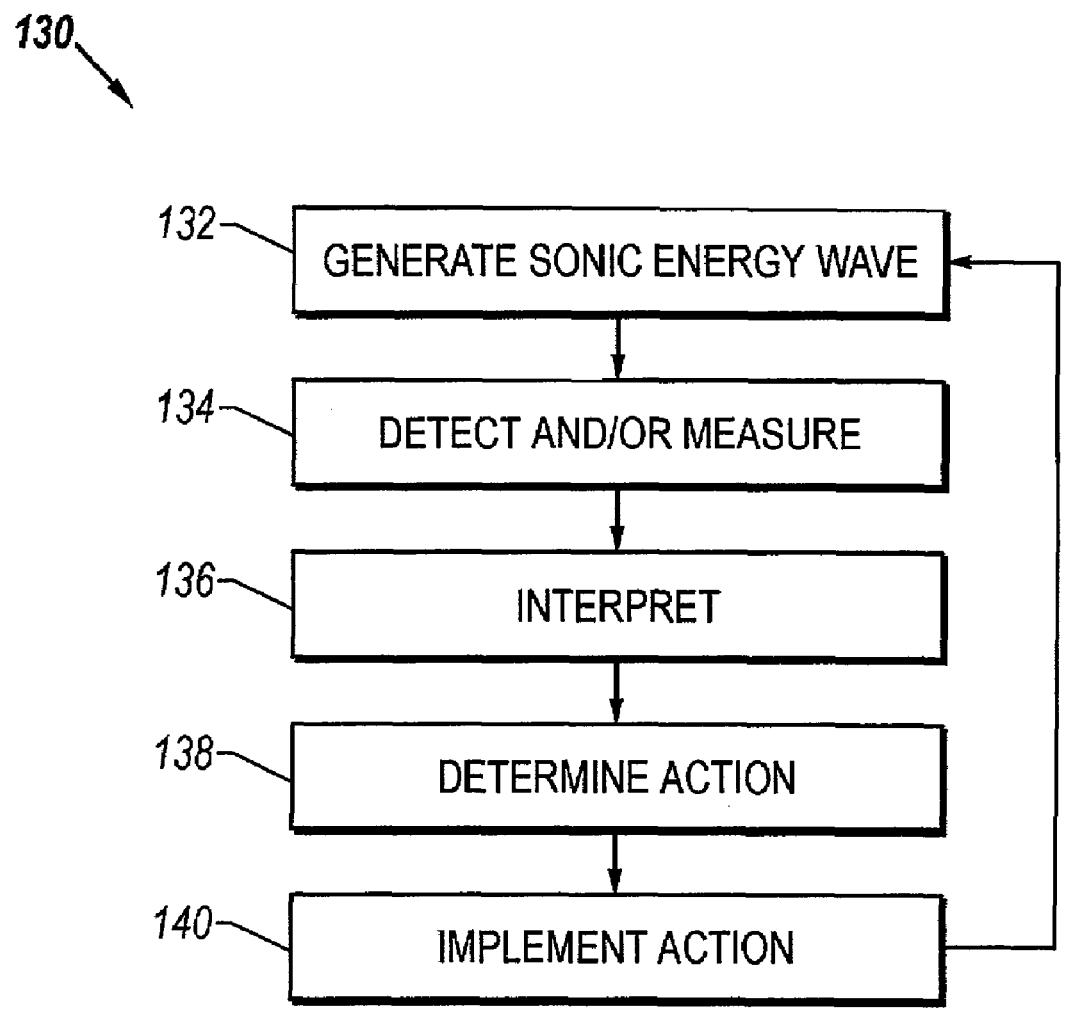
FIG. 7 is a block flow diagram of an exemplary method for use by the system of FIG. 2.

FIG. 7 is a block flow diagram of an exemplary method for use by the system as seen in FIG. 2. In the method 130, a sonic energy wave may be generated about a test object as seen in a block 132. The sonic energy wave may, for example, be generated by directing a beam of coherent electromagnetic energy at the object. However, various means of generating sonic energy waves may be envisaged.

As seen in a block 134, the sonic energy wave may be detected and/or measured by a measuring device. For example, the sonic energy wave may be measured with an interferometer. However, various methods for measuring sonic energy waves may be envisaged.

An interpreter or analyzer may interpret a signal from the measuring device as seen in a block 136. The interpreter or analyzer may use various methods to determine a result. These methods may include regression of parameters from data, determination of the location or amplitude of a peak, and/or comparison of the location or amplitude of the peak to a threshold value, among others. The analysis may be performed on time domain or frequency domain data. In addition, the analysis may utilize generator parameters, object parameters, measurement device parameters, process measurements, and/or process variables, among others.

From the interpretation, a controller or control system may determine an action as seen in a block 138. This action may be to alter a parameter associated with the process. Alternately, the action may relate to the sonic generator, the measurement device, or other process variables. The control system may implement the action as seen in a block 140 to alter the frequency of a laser beam to compensate for beam attenuation, Doppler distortion, or noise, among others. In a further example, the action may to alter a characteristic of measuring device. Further, the action may be an alarm or alert. However, various actions may be envisaged.

Figure 8:
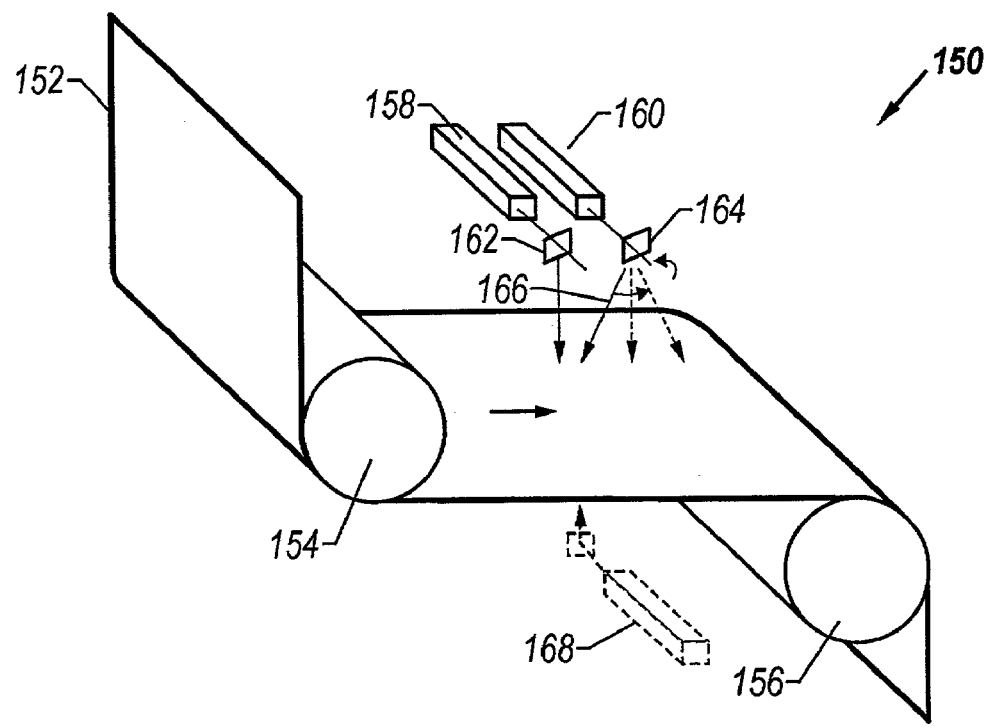
FIG. 8 is a schematic block diagram of an exemplary embodiment of the system as seen in FIGS. 1 and 2.

FIG. 8 is a schematic block diagram of an exemplary embodiment of the system as seen in FIGS. 1 and 2. In this embodiment 150, a paper sheet 152 may travel across two rollers 154 and 156. A laser generator 158 may generate a beam which impinges the paper causing ultrasonic waves. Another beam may be generated in association with a measuring device such as an interferometer.

In one embodiment, the beam may be directed along the paper sheet with a rotating mirror 164. For example, the beam may de directed a single location on the sheet as the paper moves. Alternately, the beam may be directed to a location through which paper travels. The beam may reflect from the paper to the measuring device 160. The measuring device 160 may derive a signal associated with the ultrasonic waves. From the signal, a control system may determine and implement a control action such as varying the tension between the rollers, lamination parameters, or other process parameters, among others. Alternately, the control system may manipulate the generation time of the generating and/or measuring beams. Further, the control system may manipulate beam characteristics.

For example, in the case of a measuring beam remaining on a location of the paper as the paper moves, the travel distance of the beam varies. A normal component of this travel distance may produce an apparent Doppler effect. The control system may manipulate characteristics of the measuring beam before and/or after the beams impinging to adjust for the Doppler effect.

In addition, a second measuring device 168 may be used. This measuring device 168 may direct a beam to an opposite side of the paper sheet. Alternately, the second measuring device 168 may direct the beam to the same side. Further, the sonic generation laser may direct a beam to the opposite or same side as the first measuring device 160. The sonic generator may also direct a beam to the same location as one measuring device, coaxial with a measuring device beam, or separate, among others. However, various configurations and/or combinations may be envisaged.

Figure 9:
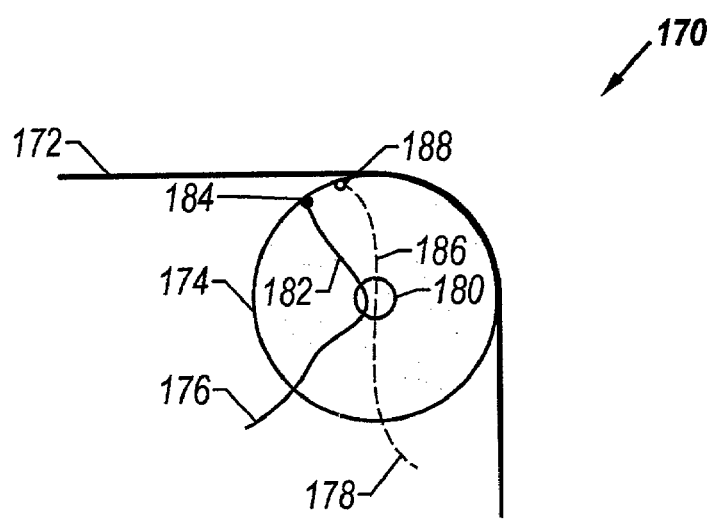
FIG. 9 is a schematic block diagram of another exemplary embodiment of the system as see in FIGS. 1 and 2.

FIG. 9 is a schematic block diagram of another exemplary embodiment of a system as seen in FIGS. 1 and 2. In this embodiment 170, a generator and or measuring device may be embedded in a roller or drum. For example, the paper 172 may traverse the surface of a rotating cylinder 174. A fiber optic cable 176 may carry a generation beam through a rotatable coupler 180 to another cable 182 and embedded coupler 184. The embedded coupler 184 may, for example, perforate through the drum and associate flush with the outer surface. In this manner, the generating beam may be directed to the sheet. A second fiber 178 may carry a measuring beam through the coupler 180 and a fiber 186 to another embedded coupler 188. The coupler 188 may also act as a collector. In this manner, the distance between the generation of the sonic energy waves and the measurement of the waves is constant. Further, the paper sheet does not move relative to the locations of the generating beam and the measuring beam. However, various configurations may be envisaged.

As such, a system and method for process control of paper manufacturing is described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. An apparatus for determining and implementing a control action associated with a characteristic of paper in a manufacturing process, the apparatus comprising:
    a first coherent electromagnetic energy source, the first coherent electromagnetic energy source producing a generator beam of coherent electromagnetic energy, the generator beam of coherent electromagnetic energy impinging the paper and generating a sonic energy signal about the paper;
    a second coherent electromagnetic energy source, the second coherent electromagnetic energy source producing a measuring beam of coherent electromagnetic energy, wherein the measuring beam of coherent electromagnetic energy is coaxially applied to the paper with the generator beam of coherent electromagnetic energy, the measuring beam of coherent electromagnetic energy impinging the paper, the measuring beam of coherent electromagnetic energy reflecting from the paper as a scattered electromagnetic energy, the scattered electromagnetic energy having a modulation associated with the sonic energy signal;
    an interferometer, the interferometer collecting part of the scattered electromagnetic energy and deriving a signal indicative of the sonic energy signal from the scattered electromagnetic energy;

an interpreter, the interpreter determining the characteristic associated with the paper from the signal indicative of the sonic energy signal;

a controller, the controller determining a control action associated with the characteristic associated with the paper; and an optical amplifier operable to amplify the scattered electromagnetic energy prior to the interferometer.

2. The apparatus of claim 1 wherein the first coherent electromagnetic energy source is a $CO_2$ laser.

3. The apparatus of claim 1 wherein the second coherent electromagnetic energy source is a ND:YAG laser.

4. The apparatus of claim 1 wherein the characteristic associated with the paper is associated with thickness.

5. The apparatus of claim 1 wherein the characteristic associated with the paper is associated with bending stiffness.

6. The apparatus of claim 1 wherein the characteristic associated with the paper is associated with out-of-plane shear rigidity.

7. The apparatus of claim 1 wherein the controller initiates the producing of the generator beam of coherent electromagnetic energy.

8. The apparatus of claim 1 wherein the controller initiates the producing of the measuring beam.

9. The apparatus of claim 1 wherein the interpreter utilizes information associated with the velocity of the paper to determine the characteristic of the paper.

10. A method for determining and implementing a control action associated with a characteristic of paper in a manufacturing process, the method comprising:

producing a generator beam of coherent electromagnetic energy with a first coherent electromagnetic energy source, the generator beam of coherent electromagnetic energy impinging the paper and generating a sonic energy signal about the paper;

producing a measuring beam of coherent electromagnetic energy with a second coherent electromagnetic energy source, wherein the measuring beam of coherent electromagnetic energy is coaxially applied to the paper with the generator beam of coherent electromagnetic energy, the measuring beam of coherent electromagnetic energy impinging the paper, the measuring beam of coherent electromagnetic energy reflecting from the paper as a scattered electromagnetic energy, the scattered electromagnetic energy having a modulation associated with the sonic energy signal;

collecting part of the scattered electromagnetic energy with an interferometer;

deriving a signal indicative of the sonic energy signal from the scattered electromagnetic energy;

determining with an interpreter the characteristic associated with the paper from the signal indicative of the sonic energy signal;

determining with a controller a control action associated with the characteristic associated with the paper; and optically amplifying the scattered electromagnetic energy prior to the interferometer.

11. The method of claim 10 wherein the first coherent electromagnetic energy source is a $CO_2$ laser.

12. The method of claim 10 wherein the second coherent electromagnetic energy source is a ND:YAG laser.

13. The method of claim 10 wherein the characteristic associated with the paper is associated with thickness.

14. The method of claim 10 wherein the characteristic associated with the paper is associated with bending stiffness.

15. The method of claim 10 wherein the characteristic associated with the paper is associated with out-of-plane shear rigidity.

16. The method of claim 10, the method further comprising:

initiating the generator beam of coherent electromagnetic energy with the controller.

17. The method of claim 10, the method further comprising:

initiating the measuring beam of coherent electromagnetic energy with the controller.

18. The method of claim 10 wherein the interpreter utilizes information associated with the velocity of the paper to determine the characteristic of the paper.

19. The apparatus of claim 1, further comprising an optical isolator to prevent feedback into the optical amplifier.

20. The method of claim 10, further comprising preventing reflected phase modulated light feedback into the optical amplifier with at least one optical isolation assembly placed in the path of propagation of the scattered electromagnetic energy.

* * * * *